United States Patent [19]

Renner

[11] 4,133,955
[45] Jan. 9, 1979

[54] PROCESS FOR THE PRODUCTION OF 2-EQUIVALENT YELLOW COUPLERS

[75] Inventor: Günter Renner, Cologne, Germany

[73] Assignee: AGFA-Gevaert Aktiengesellschaft, Germany

[21] Appl. No.: 730,204

[22] Filed: Oct. 6, 1976

[30] Foreign Application Priority Data

Oct. 11, 1975 [DE] Fed. Rep. of Germany ...... 2545756

[51] Int. Cl.$^2$ ...................... C07D 253/08; G03C 1/40
[52] U.S. Cl. ................................. 544/183; 96/100 R; 96/100 N; 548/343; 548/321; 260/326 N; 260/559 T; 544/287; 544/286; 546/142
[58] Field of Search .............................. 96/100 N, 100; 260/256.4 Q, 326 N, 559 T; 548/343, 321; 544/183

[56] References Cited

U.S. PATENT DOCUMENTS

| | | | |
|---|---|---|---|
| 3,617,291 | 11/1971 | Sawdey | 96/100 N |
| 3,928,040 | 12/1975 | Shimaumura et al. | 96/100 N |
| 3,933,500 | 1/1976 | Shiba et al. | 96/100 N |
| 4,049,458 | 9/1977 | Boie et al. | 96/100 N |
| 4,057,432 | 11/1977 | Fujiwhara et al. | 96/100 N |

*Primary Examiner*—John M. Ford
*Attorney, Agent, or Firm*—Connolly and Hutz

[57] ABSTRACT

A one-stage process for the production of a 2-equivalent acylacetamide yellow coupler, in which one hydrogen atom of the α-methylene group of the acyl acetamide coupler molecule is substituted by a group which is attached through an oxygen or nitrogen atom and which can be split off during chromogenic development with an oxidized color developer containing a primary aromatic amino group, which process is carried out by reacting a 4-equivalent acylacetamide yellow coupler with
    a compound containing an aromatic hydroxyl group or an —NH— group in a heterocyclic ring
    in the presence of a halogen, or an agent which releases halogen, and
    a basic condensation agent
    in a substantially aprotic solvent.

9 Claims, No Drawings

PROCESS FOR THE PRODUCTION OF 2-EQUIVALENT YELLOW COUPLERS

This invention relates to a new method of producing 2-equivalent yellow couplers.

In color photographic materials, open-chain keto methylene compounds, preferably acyl acetamides and, in particular, acyl acetanilides, are known to be yellow-forming color couplers (cf. the book by Mees and James entitled "The Theory of the Photographic Process", 3rd Edition 1966, pages 388 to 389).

The above-mentioned yellow color couplers may be used in the form of so-called 4-equivalent yellow couplers, in which case they require about 4 equivalents of developed silver halide for the chromogenic development of 1 mole of yellow image dye, or in the form of 2-equivalent yellow couplers, in which case they usually only require 2 equivalents of developed silver halide for the chromogenic development of 1 mole of yellow image dye. In contrast to the 4-equivalent couplers, the 2-equivalent couplers contain in the coupling position a radical which can be split off during chromogenic development.

The advantages of 2-equivalent color couplers in photography are known. Since they require less silver halide for development, the photographic layers used with them can be thinner, which not only saves silver but also increases photographic sharpness and resolving capacity.

In practice, compounds of the type which, in the coupling position, contain a spittable group attached through oxygen or nitrogen to the carbon atom of the activated methylene group of the acyl acetamide yellow coupler molecule, have proved to be effective 2-equivalent yellow couplers.

Hitherto, couplers of this kind have been produced from the corresponding 4-equivalent couplers in a two-stage reaction, in the first stage of which the 4-equivalent coupler is reacted with a halogenating agent to form the α-halogen acyl acetamide coupler, and in the second stage the halogen atom from the coupling position of the α-halogen acyl acetamide yellow coupler is exchanged by a substitution reaction with the corresponding oxygen- or nitrogen-containing group.

Offenlegungsschrift No. 2,263,587 and U.S. Pat. Nos. 2,728,658 and 3,730,722 describe the production of α-bromacyl acetamide yellow couplers. Unfortunately, the brominated coupler compounds obtained by the known processes are very difficult to purify because they generally have low melting points and because the number and quantity of secondary products formed is relatively large, especially in cases where the reaction is carried out with N-bromosuccinimide.

The method for producing an α-chloroacyl acetamide yellow coupler compound described in Offenlegungsschrift No. 2,263,587 and in U.S. Pat. No. 2,728,658 also has its disadvantages because the sulfuryl chloride used for the reaction and its byproducts produced on reaction, which by-products consist essentially of $H_2SO_4$, $SO_2$ and HCl, are difficult to remove and in addition relatively long times are required for the reaction and for working up.

As already mentioned, the α-halogen compounds obtained by the methods mentioned above first have to be carefully purified and are then reacted in a second reaction to form the corresponding 2-equivalent couplers, as described in Offenlegungsschrift No. 2,329,587; in U.S. Pat. Nos. 3,644,498 and 3,730,722 and British Pat. Nos. 1,331,179; 1,402,511 and 1,351,142. According to these publications, phenols or heterocyclic compounds are reacted with the α-halogen couplers in an aprotic solvent, for example acetonitrile, in the presence of a basic condensation agent to form the 2-equivalent couplers which contain the spittable radical attached through oxygen or nitrogen in the coupling position.

Generally, these methods are accompanied by undesirable side reactions, depending both upon the type of base used and upon the reaction temperature, higher reaction temperatures generally promoting the formation of byproducts.

It is accordingly, an object of the present invention to provide a new method which enables the required yellow coupler compounds to be simply obtained by a one-stage process.

According to the present invention a process is provided for the production of 2-equivalent acyl acetamide yellow coupler, which process comprises reacting a 4-equivalent acyl acetamide yellow coupler compound the α-methylene group of which is unsubstituted, with a compound containing the desired aromatic hydroxyl group or an —NH—group in a heterocyclic ring, and conducting the reaction in the presence of a halogen or an agent capable of liberating a halogen, as well as a basic condensation agent, the reaction being carried out in a substantially aprotic solvent. The required 2-equivalent yellow coupler is formed in a one-stage reaction accompanied by the elimination of hydrogen halide, the NH—or OH—group-containing compound supplying the splittable group. This splittable group splits off during chromogenic development, by reaction with the oxidation product of the primary aromatic amine used as color developer.

By comparison with the two-stage reaction methods of known processes, the process according to the present invention gives purer products quickly in a one-stage process.

The OH— and NH—containing compounds reacted in accordance with the present invention are essentially of the type which contain aromatic hydroxyl groups, or are cyclic compounds in which the abovementioned NH-group forms part of a heterocyclic ring.

The hydrogen atom in these OH— or NH—groups to be reacted in accordance with the present invention is sufficiently acid in order, when catalyzed with bases in the presence of halogen or halogen-releasing agents, to effect the desired substitution on the α-methylene group of acyl acetamide compounds in a one-stage process.

In general, the reaction according to the present invention is carried out by initially introducing the acyl acetamide compound and the OH— or NH—group-containing compound together with a base into a substantially aprotic solvent and slowly adding an equimolar quantity of a halogen or of a halogen-releasing compound at a temperature of preferably from −20° C. to 100° C. and more especially at a temperature of from 0° C. 20° C. However, it is of course also possible, if desired, to change the order in which the acyl acetamide compound and base are added, whereby alternatively the base or the acylacetamide compound is added slowly and the halogen or the halogen-releasing compound is introduced initially together with the remaining reactants.

Halogens suitable for use in the process according to the invention are, in particular, bromine or iodine. Examples of halogen or halogen-releasing agents suitable for use in accordance with the invention are Br$_2$, I$_2$ and mixtures of halides with oxidizing agents which are capable of releasing the halogens from the halides, such as KI and H$_2$O$_2$ or KI and Br$_2$.

In cases where molecular halogen is used, a minimum equimolar quantity of the halogen, based on the quantity of acyl acetamide compound used, is employed for the reaction according to the invention. In cases where mixtures of halides and oxidizing agents which are capable of liberating the halogen are used, a minimum of an euimolar quantity of the oxidizing agent is required, based on the acyl acetamide compound used. The quantity of halide used may be smaller because in the presence of oxidizing agents the halide, even in small traces, initiates the reaction according to the invention and is reformed again. More oxidizing agent in the reaction mixture then liberates new halogen.

Examples of aromatic hydroxyl-group-containing compounds are, in particular, phenols substituted by acyl, carbamyl or sulfamyl radicals in para-position to the phenolic hydroxyl group, the acyl groups optionally being derived from monoesters of carbonic acid and from aromatic or aliphatic sulfonic acids or carboxylic acids, such as 4-carbamyl phenol, 4-(N-alkyl-aralkyl- or aryl-, mono- or disubstituted sulfamyl)-phenol, 4-acetyl phenol or 4-(4-hydroxyphenyl sulfonyl -phenol and the like.

Examples of —NH—group-containing heterocyclic compounds are saturated, partially saturated or aromatic heterocyclic compounds which may be 5-membered or 6-membered and which may contain a —CO-,

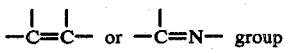

adjacent the nitrogen atom. The heterocyclic groups of such compounds may be monocyclic or may contain fused rings. Preferred compounds are 5-membered or 6-membered cyclic amides or acid imides of carboxylic acids and/or sulphonic acids, or 5-or 6-membered heterocyclic rings having at least one nitrogen atom and a

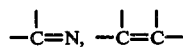

or —CO— group adjacent the nitrogen atom and which may have a benzene ring fused thereto.

Compounds particularly suitable for the reaction according to the invention are phenolic compounds and heterocyclic compounds of the type which are not themselves halogenated by the halogenating agent apart from at the point of attachment to the coupler molecule. Accordingly, preferred heterocyclic compounds are those of which the reactivity with halogenating agents is reduced to such an extent, by selecting suitable substituents such as —CO— groups or electrophilic radicals, that halogenation of the nucleus is not possible.

Examples of phenols or —NH—group-containing heterocyclic compounds suitable for use in accordance with the invention are described in French Patent Specification No. 1,411,384; in Offenlegungsschrift Nos. 2,433,812; 2,329,587; 2,363,675; 2,441,779 and 2,442,703; U.S. Pat. No. 3,730,722 and British Pat. Nos. 1,331,179; 1,386,151 and 1,351,424; 1,402,511.

Some examples of compounds suitable as splittable groups are given in Table I below:

Table I.

Compounds

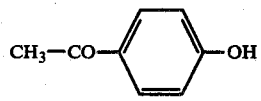

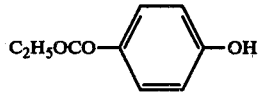

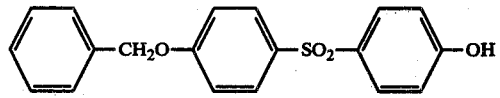

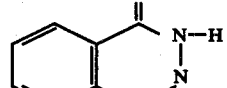

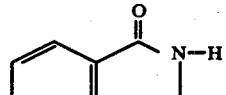

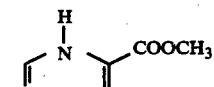

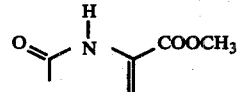

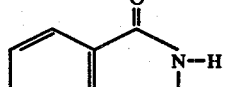

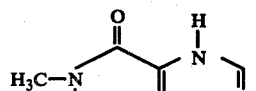

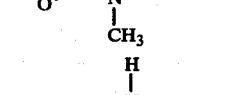

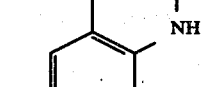

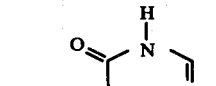

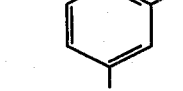

-continued
Table I.

Compounds

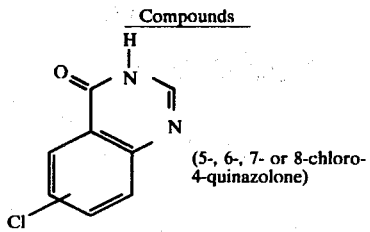

(5-, 6-, 7- or 8-chloro-4-quinazolone)

According to the present invention, substitution on the α-C-atom of the acyl acetamide compounds by the compounds containing phenolic OH-groups or by the acid-NH-containing heterocycles, is highly selective so that very few byproducts are formed, high yields are obtained and the reaction time can be greatly reduced by comparison with conventional methods. The isolated reaction products have a high degree of purity.

Accordingly, the invention provides a method of producing α-substituted-α-acyl acetamides by reacting an α-acyl acetamide, corresponding in particular to the following formula:

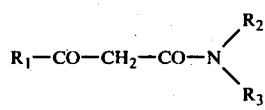

in which $R_1$, $R_2$ and $R_3$ represent groups which are normally used for acyl acetamide yellow couplers, with an —NH— or OH-group-containing compound in the presence of a halogen or halogen-releasing agent and a basic condensation agent in a substantially aprotic solvent.

Examples of $R_2$, $R_2$ and $R_3$ are groups which are generally known in acyl acetamide yellow couplers, such as for example color couplers of the type described in U.S. Pat. Nos. 3,056,675; 3,369,899, 3,393,040; 3,393,041; 3,409,439; 3,619,190; 3,645,742; 3,660,095 and 3,725,072; in Belgian Patent Specification No. 717,841 and in Offenlegungsschrift Nos. 2,002,378; 2,114,576; 2,114,577 and 2,114,578.

In particular $R_1$, $R_2$ $R_3$ may represent one of the following groups:

$R_1$ a straight-chain or branched alkyl group having in particular 1 to 18 carbon atoms, preferably a pivaloyl group, or an optionally substituted phenyl group which may contain on or more subsitutuents, such as alkyl, alkoxy, aralkyl, aryl, aroxy, sulfo, carboxy, halogen, acyl, acyloxy, acylamino, amino, carbamyl or sulfamyl which may in turn be substituted by alkyl, aryl, aralkyl or heterocyclic radicals; $R_2$ hydrogen or an alkyl group having 1 to 5 carbon atoms, for example methyl; and $R_3$—an alkyl group having 1 to 18 carbon atoms, a heterocyclic group, such as 2-thiazolyl or preferably an aryl group, such as a phenyl group which may be substituted by one or more of the substituents mentioned in reference to $R_1$.

Where one of the radicals $R_1$ and $R_3$ represents or contains alkyl, the radicals in question are alkyl radicals having 1 to 18 carbon atoms. Where one of the radicals $R_1$ and $R_3$ represents or contains acyl, the radicals in question are acyl radicals which may be derived from aliphatic or aromatic monoesters of carbonic acid or from aliphatic or aromatic carboxylic or sulfonic acids.

The 2-equivalent yellow couplers produced in accordance with the invention are, of course, preferably derived from known color couplers which have excellent properties in regard to the light absorption characteristics and stability levels of the dyes produced from them during photographic color development.

It is particularly preferred to use pivaloyl acetanolides and benozyl acetanilides with 1 to 3 substituents of the kind defined above in the anilide moiety, preferably in the 2-, 4- and 5-position, for the reaction according to the present invention.

The reaction according to the invention is carried out while the reactants are stirred in a suitable aprotic solvent at temperature of from −20 to 100° C. and preferably at a temperature below room temperature.

Reaction temperatures of from −5° C. to +20° C. have proved to be particularly suitable, depending upon the bases and couplers and the OH- or NH-containing compounds used.

The solvents used for the process according to the invention are substantially aprotic solvents such as toluene, benzene, ether and the like, or preferably polar aprotic solvents such as hexamethyl phosphoric acid triamide, dimethyl formamide, acetonitrile, acetone, ethyl acetate or mixtures thereof.

The quantity of solvent used is not critical and is governed by the solubility of the reactants in the solvent.

The OH- or NH-containing compound is generally used in at least equimolar quantities based on the acyl acetamide compounds. In general, an addition of from 1 to 3 moles of the OH-group- or NH-group-containing compound, preferably from 1.3 to 1.8 moles, based on 1 mole of the acyl acetamide compound used, has proved to be suitable for the reaction according to the invention.

Suitable basic condensation gents are substantially anydrous alkali metal hydroxides or alkali metal alcoholates, such as solid powdered sodium hydroxide or sodium methylate or potassium-tert-butylate. It is also possible to use alkali metal hydrides, such as sodium hydride, or tertiary manines, in particular aliphatic amines such as triethyl amine and N,N,N',N'-tetramethyl guanidine, as basic condensation agents.

Such bases are generally used in more than two times the molar quantity, relative to the acyl acetamide compound. Quantities of from 2 to 6 moles, preferably from 3 to 4 moles, of base per mole of acyl acetamide compound have proved to be suitable.

The process according to the invention is described by way of example in the following:

1 mole of an acyl acetamide coupler and 1.5 moles of a quinazolineone was dissolved with 3 moles of sodium methylate in 100 ml of hexamethyl phosphoric acid triamide. The solution is then cooled to 0° C. followed by the gradual dropwise addition, with stirring, of 1 mole o bromine.

On completion of the addition, the reaction mixture is stirred for another 30 minutes without further cooling.

The reaction mixture is then poured onto a mixture of ice/HCl and the resulting deposit is filtered under suction and washed. The reaction product is then taken up in ethyl acetate, neutralized with sodium hydrogen carbonate and dried with sodium sulfate. After the drying agent has been filtered off under suction and the ethyl acetate has been removed in vacuo, the product obtained is recrystallized from a solvent such as toluene or methanol.

The yellow coupler produced in accordance with the invention may be isolated from the reaction medium not only in the manner described above, but also in any other conventional manner as by pouring the reaction mixture into water, acetic acid or dilute sulfuric acid and purifying the reaction product obtained in the usual way by recrystallisation.

Examples of 2-equivalent coupler compounds produced in accordance with the invention are given in Table II below:

Table II.

A.

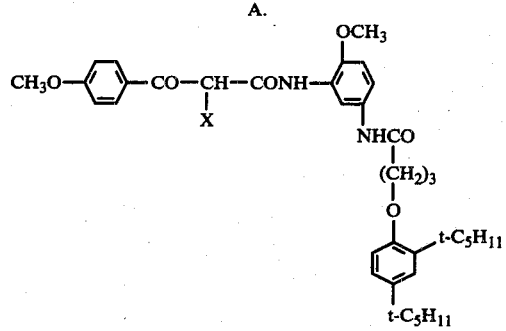

where X is

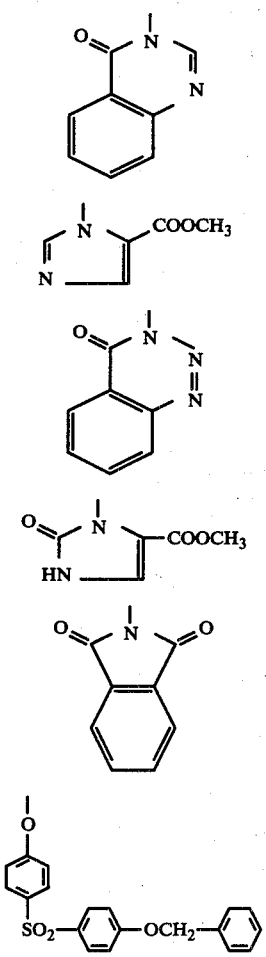

B.

-continued
Table II.

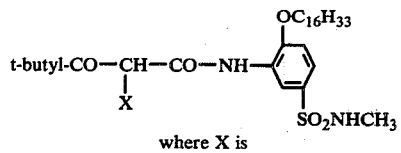

where X is

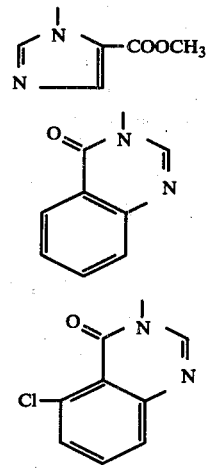

C.

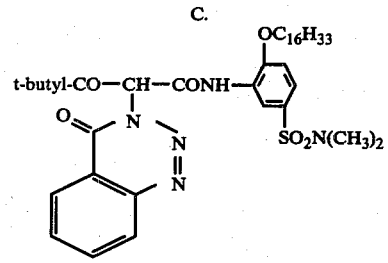

The process according to the invention is further illustrated by the following few special Examples:

Production of Compound 1:

a. 6.16 g of 2-methoxy-5-)2',4'-di-t-amylphenoxy)-butyramido-p-methoxy benzoyl acetanilide, 2.0 g of quinazolinone and 1.62 g of sodium methylate were dissolved in 100 ml of hexamethyl phosphoric acid triamide and the resulting solution was cooled to 0° C. 1.6 g of bromine were then slowly added dropwise to this mixture at 0° C. The mixture was then stirred for 30 minutes without further cooling.

The reaction mixture was worked up in known manner. Recrystallization from toluene left 6.3 g of compound No. 1. Yield: 83%: mp 135 – 137° C.

b. The same reaction was carried out in acetone instead of in hexamethyl phosphoric acid traimide. Working up in the same way as in a. produced 6.0 g of compound No. 1 in a yield ≙ 78.5%.

c. The same reaction was carried out in toluene instead of in hexamethyl phosphoric acid triamide. Working up in the same way as in a. produced 6.1 g of compound No. 1 in a yield ≙ 80.0%.

d. The same reaction was carried out in triethyl amine instead o in hexamethyl phosphoric acid triamide and with 1.2 g of NaOH instead of sodium methylate. Working up in the usual way gave 5.7 g of compound No. 1 in a yield ≙ 75%.

Production of compound 6:

18.5 g of 2-methoxy-5-(2' 4'-di-t-amylphenoxy)-butyramido-p-methoxy benzoyl acetanilide and 15 g of 4-hydroxy-4' benzyloxy phenyl sulfonyl benzene were dissolved with 4.5 g of sodium methylate in 200 ml of hexamethyl phosphoric acid triamide and the resulting solution was cooled to 0° C. A solution of 7.6 g of iodine in 50 ml of hexamethyl phosphoric acid triamide was then added dropwise with stirring to this reaction mixture. On completion of the addition, the reaction temperature was increased to room temperature, after which the reaction mixture was worked up in the usual way. The crude product was purified by dissolution in and crystallization from acetonitrile. Yield: 22.6 g of compound No. 6 (79%), mp 188–190° C.

Production of compound 9:

27.6 g of 2-hexadecyloxy-5-methylaminosulfonyl pivaloyl acetanilide, 13.5 g of 5 chloroquinazoline and 6 g of powdered NaOH were dissolved in 300 cc of acetonitrile. A solution of 8.0 g of bromine in 30 cc of acetonitrile was added dropwise to the resulting solution at +5° C. On completion of the addition, the reaction mixture was heated to room temperature. It was then filtered and the filtrate was concentrated by evaporation and subsequently worked up in the usual way.

The crude product obtained was dissolved in and crystallized from methanol. Yield: 29.7 g of compound No. 9 or ≙ 81%.

Production of compound 10:

22.4 g of 2-hexadecyloxy-5-dimethyl aminosulfonyl pivaloyl acetanilide, 9.0 g of benztriazinone and 7.5 g of sodium methylate were dissolved in 250 ml of hexamethyl phosphoric acid triamide. A solution of 6.4 g of bromine in 50 ml of dimethyl formamide was added dropwise to the resulting solution at 0° C. On completion of the addition, the reaction mixture was heated to room temperature and subsequently worked up in the usual way. The crude product was twice dissolved in and allowed to crystallize from alcohol. Yield: 23 g of compound No. 10 (83%), mp 100–102° C.

I claim:

1. In the process of converting a photographic 4-equivalent acyl acetamide yellow coupler to a 2-equivalent yellow coupler by a treatment that includes a reaction with a splittable-group-containing compound under basic condensation conditions that cause the active methylene carbon of the acyl acetamide to be substituted with a phenoxy or a heterocyclic

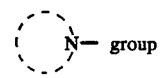

which will split off during chromogenic photographic development, the improvement according to which the conversion to a 2-equivalent coupler is effected in a single reaction stage by reacting the 4-equivalent coupler in a substantially aprotic solvent with the splittable-group-containing compound, and a halogen under the basic condensation conditions to cause the splittable group to substitute directly on the active methylene of the 4 -equivalent coupler.

2. The combination of claim 1 in which the halogen is bromine or iodine.

3. The combination of claim 1 in which the halogen is formed in situ.

4. The combination of claim 3 in which the halogen is formed by the interaction of a halide with an oxidizing agent that liberates the halogen from the halide.

5. The combination of claim 1 in which the reaction is effected at a temperature of from −20° C. to +100° C.

6. The combination of claim 2 in which the reaction is effected at a temperature from +5° C. to +20° C.

7. The combination of claim 1 in which the solvent is substantially a polar solvent.

8. The combination of claim 1 in which the splittable-group containing compound is a phenol substituted in paraposition by an acyl, carbamyl or sulfamyl radical.

9. The combination of claim 1 in which the splittable-group-containing compound has a 5- or 6-membered heterocyclic ring of carbon and nitrogen atoms with an NH adjacent to a

or —CO— structure.

* * * * *